United States Patent

Stahle et al.

[11] 4,036,972
[45] July 19, 1977

[54] 2-(N-THIENYLMETHYL-PHENYLAMINO)-IMIDAZOLINES-(2) AND SALTS THEREOF

[75] Inventors: Helmut Stahle; Herbert Koppe; Werner Kummer; Klaus Stockhaus, all of Ingelheim am Rhein, Germany

[73] Assignee: Boehringer Ingelheim GmbH, Ingelheim am Rhein, Germany

[21] Appl. No.: 607,258

[22] Filed: Aug. 25, 1975

Related U.S. Application Data

[63] Continuation-in-part of Ser. No. 441,451, Feb. 11, 1974, Pat. No. 3,937,717.

[30] Foreign Application Priority Data

Feb. 23, 1973 Germany .................. 2308883

[51] Int. Cl.² .............. C07D 409/12; A61K 31/415
[52] U.S. Cl. .................. 424/273; 260/309.6; 260/564 E
[58] Field of Search .................. 260/309.6; 424/273

[56] References Cited

U.S. PATENT DOCUMENTS

| | | | |
|---|---|---|---|
| 3,147,270 | 9/1964 | Anderson | 260/309.6 |
| 3,236,857 | 2/1966 | Zeile et al. | 260/309.6 |
| 3,296,077 | 1/1967 | Berg | 260/309.6 |
| 3,746,724 | 7/1973 | Werner et al. | 260/309.6 |
| 3,758,476 | 9/1973 | Rippel et al. | 260/309.6 |
| 3,804,833 | 4/1974 | Stähle et al. | 260/309.7 |
| 3,850,926 | 11/1974 | Stähle et al. | 260/309.6 |

FOREIGN PATENT DOCUMENTS

| | | | |
|---|---|---|---|
| 1,174,349 | 12/1969 | United Kingdom | 260/309.6 |
| 1,180,766 | 2/1970 | United Kingdom | 260/309.6 |
| 1,230,482 | 5/1971 | United Kingdom | 260/309.6 |
| 1,230,583 | 5/1971 | United Kingdom | 260/309.6 |

OTHER PUBLICATIONS

Staehle et al., Chem. Abst. 1972, vol. 77, No. 126630p.
Burger et al., Medicinal Chemistry 2nd Ed., pp. 77-81, N.Y., Interscience, 1960.
Kyrides et al., J. Amer. Chem. Soc. 1947, vol. 69, pp. 2239-2240.
Urech et al., Hel. Chim. Acta 1950, vol. 33, pp. 1386-1407.
Rippel et al., Chem. Abst. 1971, vol. 74, No. 100054s.
Yasuhiko et al., Chem. Abst. 1971, vol. 75, No. 140850a.

*Primary Examiner*—Natalie Trousof
*Attorney, Agent, or Firm*—Hammond & Littell

[57] ABSTRACT

Compounds of the formula

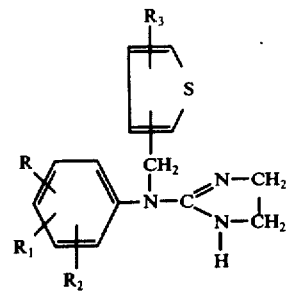

wherein
R, $R_1$ and $R_2$ are each hydrogen, fluorine, chlorine, bromine, methoxy or trifluoromethyl, but other than all hydrogen at the same time, and
$R_3$ is hydrogen, methyl or ethyl, and non-toxic, pharmaceutically acceptable acid addition salts thereof; the compounds as well as their salts are useful as analgesics and hypotensives.

11 Claims, No Drawings

2-(N-THIENYLMETHYL-PHENYLAMINO)-IMIDAZOLINES-(2) AND SALTS THEREOF

This is a continuation-in-part of copending application Ser. No. 441,451 filed Feb. 11, 1974, now U.S. Pat. No. 3,937,717 granted Feb. 10, 1976.

This invention relates to novel 2-(N-thienylmethyl-phenylamino)-imidazolines-(2) and acid addition salts thereof, as well as to methods of preparing these compounds.

More particularly, the present invention relates to a novel class of 2-phenylamino-imidazolines-(2) represented by the formula

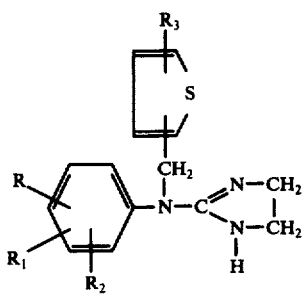

wherein
R, $R_1$ and $R_2$ are each hydrogen fluorine, chlorine, bromine, methoxy or trifluoromethyl, but other than all hydrogen at the same time, and
$R_3$ is hydrogen, methyl or ethyl,
and non-toxic, pharmaceutically acceptable acid addition salts thereof.

A preferred subgenus thereunder is constituted by those compounds of the formula I wherein the phenyl moiety is 2,6-disubstituted.

Examples of suitable acids for the non-toxic, pharmaceutically acid addition salts are mineral acids, such as hydrochloric acid, hydrobromic acid, hydroiodic acid, hydrofluoric acid, sulfuric acid, phosphoric acid and nitric acid; or organic acids, such as acetic acid, propionic acid, butyric acid, valeric acid, caproic acid, caprinic acid, oxalic acid, malonic acid, succinic acid, glutaric acid, maleic acid, fumaric acid, lactic acid, tartaric acid, citric acid, malic acid, gluconic acid, benzoic acid, p-hydroxybenzoic acid, phthalic acid, cinnamic acid, salicylic acid, ascorbic acid, 8-chlorotheophylline and methanesulfonic acid.

Examples of suitable compounds of formula I are:
2-[N-(thienyl-(2)-methyl)-N-(2,6-dichloro-phenyl)-amino]-imidazoline-(2)
2-[N-(thienyl-(3)-methyl)-N-(2,6-dichloro-phenyl)-amino]-imidazoline-(2)
2-[N-(thienyl-(3)-methyl)-N-(4-methoxy-phenyl)-amino]-imidaxoline-(2)
2-[N-(thienyl-(3)-methyl)-N-(2,6-dichloro-4-bromo-phenyl)-amino]-imidazoline-(2)
2-[N-(thienyl-(2)-methyl)-N-(2,6-dichloro-4-bromo-phenyl)-amino]-imidazoline-(2)
2-[N-(thienyl-(2)-methyl)-N-(2-trifluoromethyl-phenyl)-amino]-imidazoline-(2)
2-[N-(thienyl-(2)-methyl)-N-(2,4-dichloro-phenyl)-amino]-imidazoline-(2)
2-[N-(thienyl-(3)-methyl)-N-(2,4-dichloro-phenyl)-amino]-imidazoline-(2)
2-[N-(thienyl-(2)-methyl)-N-(2,3-dichloro-phenyl)-amino]-imidazoline-(2)
2-[N-(thienyl-(3)-methyl)-N-(2,3-dichloro-phenyl)-amino]-imidazoline-(2)
2-[N-(thienyl-(2)-methyl)-N-(2,5-dichloro-phenyl)-amino]-imidazoline-(2)
2-[N-(thienyl-(3)-methyl)-N-(2,5-dichloro-phenyl)-amino]-imidazoline-(2)
2-[N-(thienyl-(2)-methyl)-N-(2,6-dibromo-phenyl)-amino]-imidazoline-(2)
2-[N-(thienyl-(3)-methyl)-N-(2,6-dibromo-phenyl)-amino]-imidazoline-(2)
2-[N-(thienyl-(2)-methyl)-N-(2,6-difluoro-phenyl)-amino]-imidazoline-(2)
2-[N-(thienyl-(3)-methyl)-N-(2,6-difluoro-phenyl)-amino]-imidazoline-(2)
2-[N-(3-methylthienyl-(2)-methyl)-N-(2,6-dichloro-phenyl)-amino]-imidazoline-(2)
2-[N-(2-methylthienyl-(3)-methyl)-N-(2,6-dichloro-phenyl)-amino]-imidazoline-(2)
2-[N-(3-methylthienyl-(4)-methyl)-N-(2,6-dichloro-phenyl)-amino]-imidazoline-(2)
2-[N-(2-methylthienyl-(4)-methyl)-N-(2,6-dichloro-phenyl)-amino]-imidazoline-(2)
2-[N-(2-methylthienyl-(5)-methyl)-N-(2,6-dichloro-phenyl)-amino]-imidazoline-(2)
2-[N-(4-methylthienyl-(2)-methyl)-N-(2,6-dichloro-phenyl)-amino]-imidazoline-(2)
2-[N-(3-ethylthienyl-(2)-methyl)-N-(2,6-dichloro-phenyl)-amino]-imidazoline-(2)
2-[N-(2-ethylthienyl-(3)-methyl)-N-(2,6-dichloro-phenyl)-amino]-imidazoline-(2)
2[N-(3-ethylthienyl-(4)-methyl)-N-(2,6-dichloro-phenyl)-amino]-imidazoline-(2)
2-[N-(2-ethylthienyl-(4)-methyl)-N-(2,6-dichloro-phenyl-amino]-imidazoline-(2)
2-[N-(2-ethylthienyl-(5)-methyl)-N-(2,6-dichloro-phenyl)-amino]-imidazoline-(2)
2[N-(4-ethylthienyl-(2)-methyl)-N-(2,6-dichloro-phenyl)-amino]-imidazoline-(2)
2-[N-(thienyl-(2)-methyl)-N-(2,4-difluoro-phenyl)-amino]-imidazoline-(2)
2-[N-(3-methylthienyl-(2)-methyl)-N-(2,4-dichloro-phenyl)-amino]-imidazoline-(2)
2-[N-(2-methylthienyl-(3)-methyl)-N-(2,3-dichloro-phenyl)-amino]-imidazoline-(2)
2-[N-(2-ethylthienyl-(4)-methyl)-N-(2,5-dichloro-phenyl)-amino]-imidazoline-(2)
2-[N-(2-ethylthienyl-(5)-methyl)-N-(2,6-dibromo-phenyl)-amino]-imidazoline-(2)
2-[N-(2-ethylthienyl-(2)-methyl)-N-(2,6-dichloro-4-bromophenyl)-amino]-imidazoline-(2)

The compounds of the formula I may be produced by
a. reacting a 2-phenylamino-imidazoline-(2) of the formula

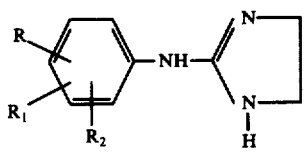

wherein R, $R_1$ and $R_2$ have the above defined meanings, with a thienylmethyl halide of the formula

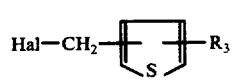

wherein Hal is chlorine, bromine or iodine and $R_3$ has the above defined meanings; or b. by reacting a compound of the formula

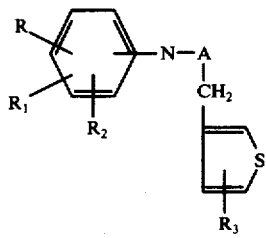

wherein R, $R_1$, $R_2$ and $R_3$ are defined as above, and A is

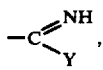

where Y is alkoxy or alkylthio with up to 4 carbon atoms, or sulfhydryl or amino, with ethylenediamine or an acid addition salt thereof.

The reaction in accordance with process (a) is appropriately effected by heating the reactants, preferably in the presence of a polar or nonpolar organic solvent, to temperatures of about 50° to 150° C. The specific reaction conditions depend to a high degree upon the reactivity of the reactants and it is recommended to use the halide in excess for alkylation and to effect the reaction in the presence of an acid-binding agent.

With process (b), it is required to work at elevated temperature of about 60° to 180° C. Solvents are not necessary but it is useful to use the ethylenediamine or its acid addition salt, which is a reactant, in excess.

Starting compounds of the formula II have been described, for example, in Belgian Pat. Nos. 623,305; 687,656; 687,657 and 705,944. Starting compounds of the formula III may be prepared by known process, such as halo-methylation of thiophenes or reduction of a thiophenecarbonate with metal hydrides to hydroxymethyl-thiophenes, and subsequent exchange of the hydroxy with halogens. Chloromethylthiophenes may be converted into corresponding bromo- or iodomethyl derivatives by reaction with alkali metal bromides or alkali metal iodides.

Compounds of the formula IV may be prepared by reacting anilines with compounds of the formula III and subsequent reaction of the secondary amines formed thereby with cyanates or thiocyanates, whereby ureas or thioureas are formed. Ureas and thioureas may then be converted further with alkylation agents into corresponding isouronium salts or isothiouronium salts. The said acid addition compounds may be reacted with bases to form the corresponding isoureas or isothioureas. By splitting off water from ureas or $H_2S$-splitting from thioureas with lead or mercury salts, cynamides are obtained to which ammonia may be added to form guanidines.

The novel analgesic compositions of the invention are comprised of an effective amount of at least one compound of the formula I or its non-toxic, pharmaceutically acceptable acid addition salts and a pharmaceutical carrier. The composition may be in the form of tablets, capsules, suppositories, solutions or powders and may contain other active ingredients. Because of their analgesic and blood pressure reducing properties, the compositions are useful for the treatment of various types of pain such as migraine headaches or for the treatment of high blood pressure.

The compositions can be prepared with known galenic excipients, carriers, disintegrating agents, lubricants or sustained release agents.

Tablets may be obtained by mixing the active ingredients with known excipients, for example, with inert diluents such as calcium carbonate, calcium phosphate or lactose; disintegrants such as corn starch or alginic acid; binders such as starch or gelatin; lubricants such as magnesium stearate or talc; and/or agents for sustained release such as carboxypolymethylene, carboxymethylcellulose, cellulose acetate phthalate or polyvinylacetate.

The tablets may also have several layers and coated tablets may be produced by coating cores prepared analogous to the tablets with agents commonly used for coating tablets such as polyvinylpyrrolidone, shellac, gum arabic, talcum, titanium dioxide or sugar. To obtain sustained release or to avoid incompatibilities, the core may also consist of several layers. The tablet-coat is preferably made of several layers to obtain sustained release whereby the auxiliaries mentioned above for the tablets may be used.

For production of soft gelatin capsules or of similar sealed capsules, the active substance may be admixed with a plant oil. Hard gelatin capsules may contain granulates of the active substance with solid carriers in powder form such as lactose, saccharose, sorbitol, mannitol, starch such as potato starch, corn starch or amylopetin, cellulose derivatives or gelatin.

Syrups of the active ingredients of the invention or active ingredient combinations may also contain a sweetener such as saccharin, cyclamate, glycerin or sugar, as well as an agent improving the taste such as flavors like vanillin or orange extract. They may also contain suspension auxiliaries or thickeners, such as sodium carboxymethylcellulose, wetting agents such as condensation products of fatty alcohols with ethylene oxide, or preservatives such as alkyl p-hydroxy-benzoates.

Injectable solutions or suspensions may be produced in the conventional way such as with the use of preservatives such as alkyl p-hydroxybenzoates, or stabilizers such as complexons and they are then added under sterile condition into injection vials or ampules. The solution may also contain stabilizers and/or buffers.

The suppositories may be produced, for example, by mixing the active ingredient or active ingredient combinations with conventional carriers such as neutral fats or polyethyleneglycol or derivatives thereof. Gelatin capsules for rectal administration containing the active substance in admixture with plant oil or paraffin oil may be produced as well.

The novel method of the invention for relieving pain and/or reducing blood pressure in warm-blooded animals comprises administering to warm-blooded animals an effective amount of at least one compound of the formula I or it non-toxic, pharmaceutically acceptable acid addition salts. The compounds may be administered parenterally or enterally. The usual daily dose is 1 to 30 mgm/kg depending upon the method of administration and the specific compound.

In the following examples there are described several preferred embodiments to illustrate the invention. However, it should be understood that the invention is not intended to be limited to the specific embodiments.

EXAMPLE 1

2-[N-(thienyl-(2)-methyl)-N-(2,6-dichloro-phenyl)-amino]-2-imidazoline

A mixture of 6.9 gm (0.03 moles) of 2-(2,6-dichlorophenylamino)-2-imidazoline, 4.4 gm (10% excess) of 2-chloromethylthiophene, 7 ml of triethylamine and 60 cc of anhydrous toluene was refluxed with stirring for 3 hours and after cooling, the mixture was varuum filtered. The recovered precipitate was dissolved in dilute hydrochloric and the resulting solution was extracted several times with ether. The aqueous phase was adjusted to different pH values with dilute sodium hydroxide solution and was extracted at each with ether. The ether fractions with a uniform thin layer chromatography were combined, dried over drierite and evaporated under reduced pressure to dryness to obtain 2.7 gm (27.6%) of 2-[N-(thienyl-(2)-methyl)-N-(2,6-dichlorophenyl)-amino]-2-imidazoline melting at 111° to 114° C. The product was soluble in organic solvents and insoluble in water.

EXAMPLE 2

Using a procedure of Example 1, a 29.4% yield of 2-[N-(thienyl-(2)-methyl)-N-(2-chloro-6-methyl-phenyl)-amino]-2-imidazoline with a melting point of 88°-90° C was obtained.

EXAMPLE 3

Using the procedure of Example 1, a 27.0% yield of 2-[N-(thienyl-(3)-methyl)-N-(2,6-dichloro-phenyl)-amino]-2-imidazoline with a melting point of 252°-254° C was obtained.

EXAMPLE 4

Using a procedure of Example 1, a 26.8% yield of 2-[N-(thienyl-(2)-methyl)-N-(4-methoxy-phenyl)-amino]-2-imidazoline with a melting point of 78° C was obtained.

EXAMPLE 5

Using a procedure of Example 1, a 22.8% yield of 2-[N-(thienyl-(2)-methyl)-N-(2,6-dichloro-4-dichloro-4-bromo-phenyl)-amino]-2-imidazoline with a melting point of 172°-174° C was obtained.

EXAMPLE 6

Using the procedure of Example 1, a 39.0% yield of 2-[N-(thienyl-(2)-methyl)-N-(2-trifluoromethyl-phenyl)-amino]-2-imidazoline with a melting point of 134°-136° C was obtained.

EXAMPLE 7

Using the procedure of Example 1, a 21.1% yield of 2-[N-(3-methylthienyl-(2)-methyl)-N-(2,6-dichloro-phenyl)-amino]-2-imidazoline with a melting point of 132°-135° C was obtained.

EXAMPLE 8

Using a procedure of Example 1, a 31.9% yield of 2-[N-(thienyl-(2)-methyl)-N-(2,4-difluoro-phenyl)-amino]-2-imidazoline in the form of an oil was obtained.

EXAMPLE A

Tablets weighing 445 mgm were prepared by intimately admixing 30 mgm of 2-[N-(thienyl-(2)-methyl)-N-(2,6-dichlorophenyl)-amino]-2-imidazoline, 160 mgm of corn starch, 250 mgm of secondary calcium phosphate and 5 mgm of magnesium stearate and the mixture was granulated and pressed into tablets containing 30 mgm of the active compound.

EXAMPLE B 1.5 parts by weight or 2[N-(thienyl-(2)-methyl)-N-(2,6-dichloro-phenyl)-amino]-2-imidazoline and 0.2 parts by weight of the sodium salt of the ethylenediaminetetraacetic acid were dissolved in sufficient water and water was added to obtain a final volume of 100.0 parts by weight. The solution was filtered free of suspended particles and filled into 2 cc ampules under aseptic conditions. Then, the ampules were sterilized and sealed and each ampule contained 20 mgm of the active ingredient.

Various modifications of the products and processes of the invention may be made without departing from the spirit or scope thereof and it is to be understood that the invention is to be limited only as defined in the appended claims.

We claim:

1. a compound of the formula

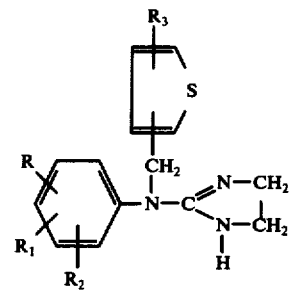

wherein R, $R_1$ and $R_2$ are each hydrogen, fluorine, chlorine or bromine, but other than all hydrogen at the same time, and $R_3$ is hydrogen, methyl or ethyl, or a non-toxic, pharmaceutically acceptable acid addition salt thereof.

2. A compound of claim 1, which is 2-[N-(thienyl-(2)-methyl)-N-(2,6-dichloro-4-bromophenyl)-amino]-2-imidazoline or a non-toxic, pharmaceutically acceptable acid addition salt thereof.

3. A compound of claim 1, which is 2-[N-(3-methyl-thienyl-(2)-methyl)-N-(2,6-dichlorophenyl)-amino]-2-imidazoline or a non-toxic, pharmaceutically acceptable acid addition salt thereof.

4. A compound of claim 1, which is 2-[N-(thienyl-(2)-methyl)-N-(2,4-difluoro-phenyl)-amino]-2-imidazoline or a non-toxic, pharmaceutically acceptable acid addition salt thereof.

5. A compound of the formula

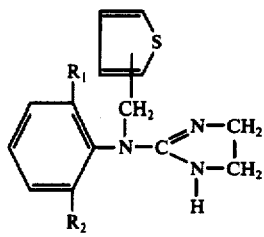

wherein $R_1$ and $R_2$ are each hydrogen, fluorine, chlorine or bromine, but other than all hydrogen at the same time, or a non-toxic, pharmaceutically acceptable acid addition salt thereof.

6. A compound of claim 5, which is 2-[N-(thienyl-(2)-methyl)-N-(2,6-dichloro-phenyl)-amino]-2-imidazoline or a non-toxic, pharmaceutically acceptable acid addition salt thereof.

7. A compound of claim 5, which is 2-[N-(thienyl-(3)-methyl)-N-(2,6-dichloro-phenyl)-amino]-2-imidazoline or a non-toxic, pharmaceutically acceptable acid addition salt thereof.

8. Analgesic compositions comprising an inert pharmaceutical carrier and an effective amount of at least one compound of claim 1.

9. A method of relieving pain in warm-blooded animals, which comprises administering to warm-blooded animals an analgesically effective amount of at least one compound of claim 1.

10. Analgesic compositions comprising an inert pharmaceutical carrier and an effective amount of at least one compound of claim 5.

11. A method of relieving pain in warm-blooded animals, which comprises administering to warm-blooded animals an analgesically effective amount of at least one compound of claim 5.

* * * * *